US009050204B2

(12) United States Patent
Hosford et al.

(10) Patent No.: US 9,050,204 B2
(45) Date of Patent: Jun. 9, 2015

(54) SYSTEM AND METHOD FOR REMOVING AN IMPLANTED OBJECT IN A PASSAGEWAY IN A PATIENT

(75) Inventors: Andrew T. Hosford, Stanford, CA (US); Siddarth Satish, Cupertino, CA (US); Logan Ames, Stanford, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 898 days.

(21) Appl. No.: 13/110,861

(22) Filed: May 18, 2011

(65) Prior Publication Data

US 2012/0123515 A1 May 17, 2012

Related U.S. Application Data (60) Provisional application No. 61/413,984, filed on Nov. 16, 2010.

(51) Int. Cl.
*A61F 2/95* (2013.01)

(52) U.S. Cl.
CPC ............ *A61F 2/95* (2013.01); *A61F 2002/9528* (2013.01)

(58) Field of Classification Search
CPC .............. A61F 2/95; A61F 2002/9528; A61F 2002/9534
USPC ......... 606/108, 191, 194, 200; 623/1.11, 1.12
See application file for complete search history.

(56) References Cited

U.S. PATENT DOCUMENTS

| | | | |
|---|---|---|---|
| 4,503,569 A | 3/1985 | Dotter | |
| 4,990,151 A | 2/1991 | Wallsten | |
| 5,098,440 A | 3/1992 | Hillstead | |
| 5,201,757 A * | 4/1993 | Heyn et al. | 606/198 |
| 5,476,510 A * | 12/1995 | Eberhardt et al. | 623/2.11 |
| 5,713,948 A | 2/1998 | Uflacker | |
| 5,910,144 A * | 6/1999 | Hayashi | 606/108 |
| 6,086,599 A | 7/2000 | Lee | |
| 6,106,531 A | 8/2000 | Schatz | |
| 6,159,219 A | 12/2000 | Ren | |
| 6,187,016 B1 | 2/2001 | Hedges | |
| 6,258,098 B1 | 7/2001 | Taylor | |
| 6,451,025 B1 | 9/2002 | Jervis | |
| 6,802,846 B2 | 10/2004 | Hauschild | |
| 6,821,291 B2 | 11/2004 | Bolea | |
| 7,476,256 B2 | 1/2009 | Meade | |
| 2005/0175703 A1* | 8/2005 | Hunter et al. | 424/486 |

* cited by examiner

*Primary Examiner* — Ashley Fishback
(74) *Attorney, Agent, or Firm* — Vista IP Law Group, LLP (57) ABSTRACT

A system for removing an implanted stent or other object from a passageway in a patient includes a housing, an expansion element that operates between an enlarged mode in which the expansion element may radially expand to a diameter larger than the object diameter and a collapsed mode in which the expansion element radially contracts, and a plurality of radially contractible members configured to circumferentially engage the implanted object. A method for moving an implanted stent or other object from an initial location in a passageway includes positioning an expansion element proximate to the stent, expanding the expansion element thereby creating a tapered annular space between the stent and the passageway, advancing a plurality of members towards the tapered annular space, engaging the stent with the members, radially contracting the members to radially compress the stent, and moving the compressed stent from the initial location.

23 Claims, 11 Drawing Sheets

FIG. 21B

SYSTEM AND METHOD FOR REMOVING AN IMPLANTED OBJECT IN A PASSAGEWAY IN A PATIENT

CROSS-REFERENCE TO RELATED APPLICATIONS

This application claims the benefit of US Provisional Application No. 61/413,984 filed 16 Nov. 2010, which is incorporated in its entirety by this reference.

TECHNICAL FIELD

This invention relates generally to the medical field, and more specifically to an improved system and method for removing an implanted object in a passageway in a patient.

BACKGROUND

Stents are used for a variety of purposes in applications such as gastrointestinal, cardiovascular, and respiratory applications. Stents are generally used to open occluded lumens of passageways, to provide support to regions of passageways with weakened walls, and in some cases, deliver drugs or other medication to a particular region of a passageway. However, some circumstances require removal and/or repositioning of a stent. For example, the stent may undergo fatigue or experience some other failure. As another example, the environment around the stent after implantation may change in such a way that the stent is either physiologically unnecessary or even dangerous (e.g., restenosis or hyperplasia). In most cases, stents are deployed in a patient with little or no intention for future removal, and accordingly are not designed for easy retrieval or repositioning. Thus, there is a need in the medical field to create an improved system and method for removing an implanted object in a passageway in a patient. This invention provides such an improved system and method.

DESCRIPTION OF THE PREFERRED EMBODIMENTS

The following description of preferred embodiments of the invention is not intended to limit the invention to these preferred embodiments, but rather to enable any person skilled in the art to make and use this invention.

System for Removing an Implanted Object

Figure 1A:
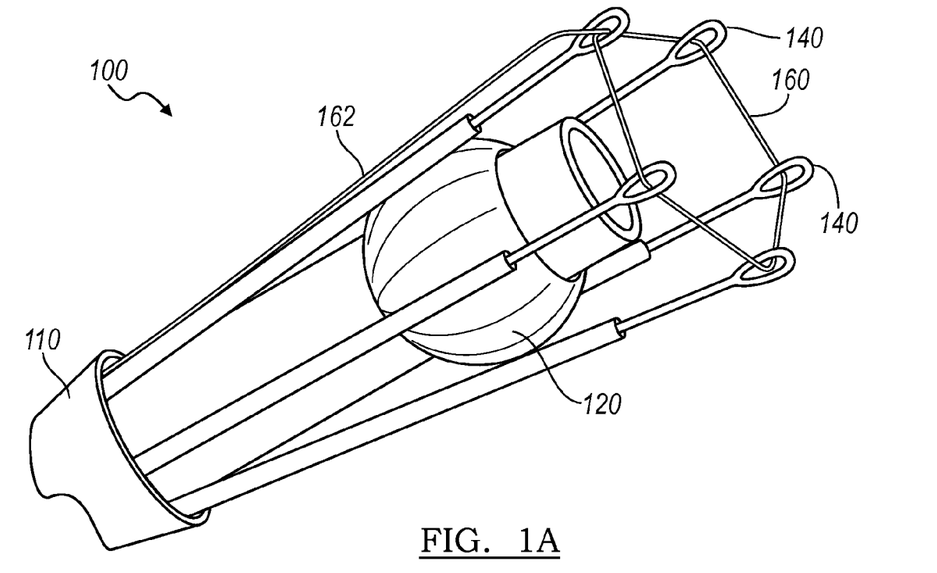
FIGS. 1-4 are schematics of the system of a preferred embodiment.
Figure 1B:
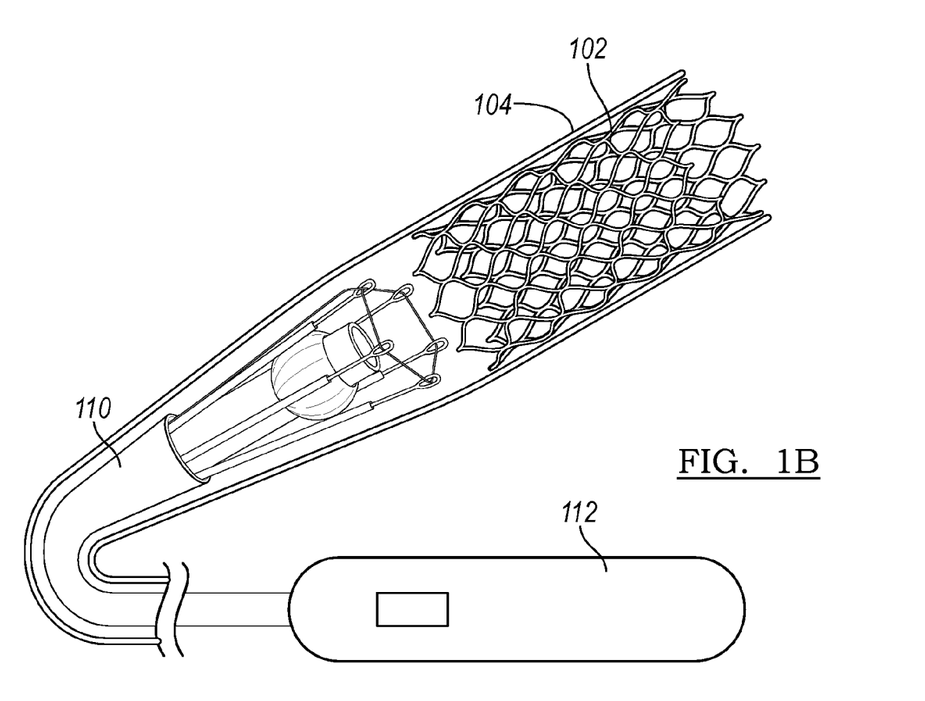
Figure 2A:
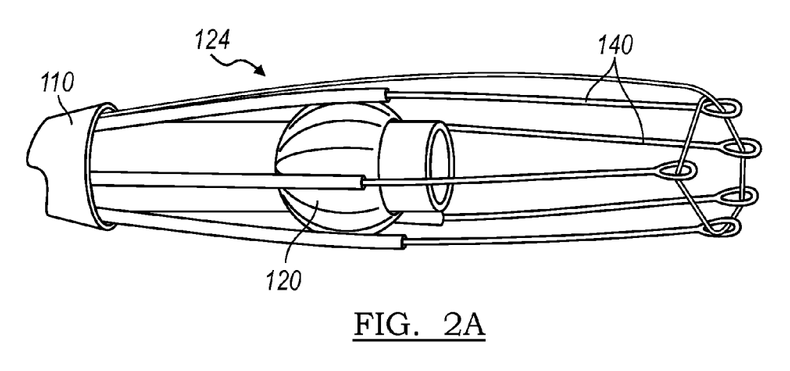
Figure 2B:
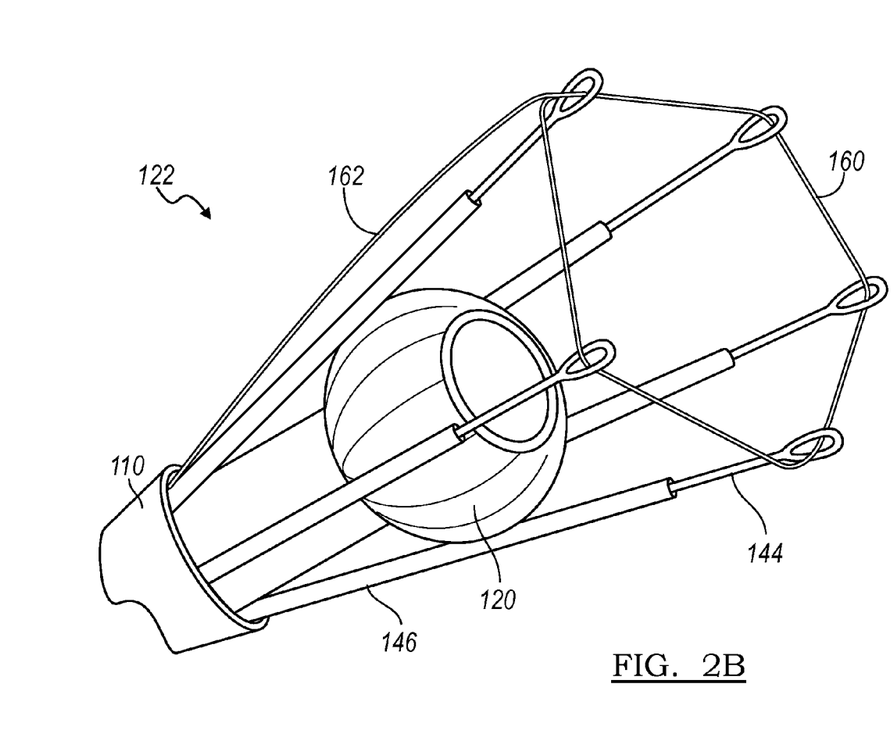
Figure 3:
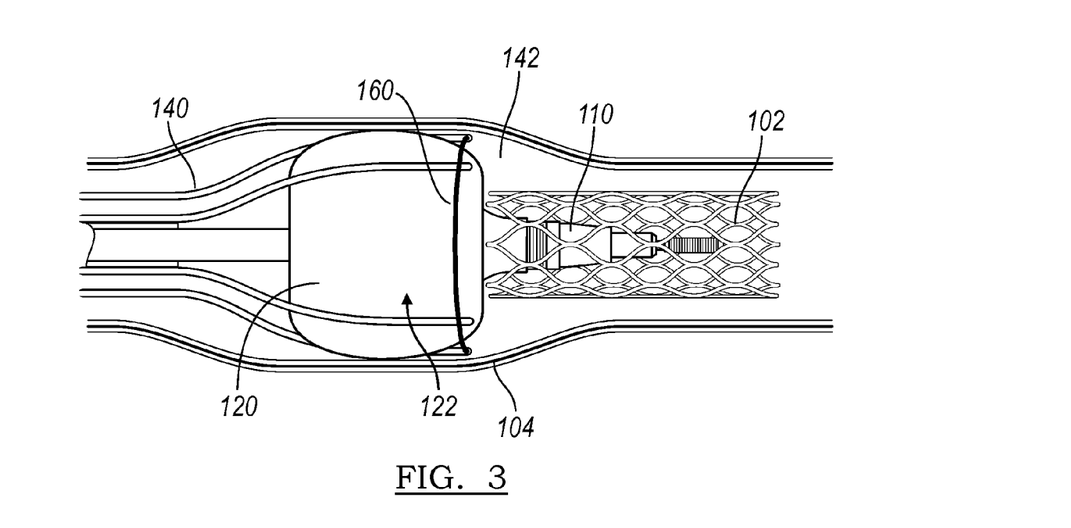

As shown in FIGS. 1 and 2, the system 100 of a preferred embodiment for removing an implanted object from a passageway in a patient includes: a housing 110 insertable in the passageway; an expansion element 120 coupled to the housing and configured to operate in an enlarged mode 122 and a collapsed mode 124; and a plurality of radially contractible members 140 configured to advance to a location longitudinally displaced from the expansion element, where the advanced plurality of members are configured to circumferentially engage the implanted object. In the enlarged mode 122, as shown in FIGS. 2B and 3, the expansion element 120 preferably radially expands to a diameter larger than the diameter of the object, such that when positioned proximate to the implanted object in the passageway (e.g. proximal or distal to the object), the enlarged expansion element creates a tapered annular space 142 between the object and the passageway. In the collapsed mode 124, as shown in FIG. 2A, the expansion element 120 radially contracts. The system 100 is preferably used to remove and/or reposition an implanted stent 102 in a passageway in a patient. In one preferred embodiment, the system is used to remove and/or reposition a stent implanted in a gastrointestinal tract (such as the esophagus), but may alternatively be used to move a stent implanted in a cardiovascular, respiratory, or any suitable biological passageway. Alternatively, although the system is primarily described in terms of removing and/or repositioning a stent, the system may be used to remove and/or reposition any suitable foreign object from any suitable passageway or other environment.

The housing 110 functions to transport the system into and through the passageway 104 to and from the implanted stent 102. As shown in FIGS. 1-2, the housing no carries the expansion element 120, the plurality of members 140, and/or any suitable system components, such that the system components are protected when the housing no is navigated through the passageway 104. For example, the housing may include at least one central cavity or side recess that contains one or more of the system components. The housing 110 is coupled to a handle 112 or other user interface outside the body of the patient or other suitable environment. In one embodiment, the housing 110 may be part of an apparatus that is insertable in the passageway and allows for navigation through the passageway. In one variation, the housing no is incorporated in or coupled to an endoscope, such as for use of the system in the gastrointestinal tract (e.g. esophagus), respiratory passages, or other suitable environments. In another variation, the housing 110 is incorporated in or coupled to a catheter. In another embodiment, the housing 110 is self-navigable, such as with an articulating tip or other mechanism that enables a user to guide the housing 110 into and through the passageway. The housing preferably has a smooth profile (e.g. no burrs, extensions, or other protrusions) and may include soft, flexible or cushioning material to reduce the possibility of incurring damage to the passageway and/or system components during navigation in the passageway. However, the housing may be coupled to or include any suitable structure for carrying the expansion element 120, the plurality of members 140, and/or any other system components within the passageway.

The expansion element 120 functions to separate at least a portion of the passageway walls 104 from the stent, when placed within the passageway proximate (e.g., proximal or distal) to the stent. When enlarged within the lumen of the stent, the expansion element 120 may additionally and/or alternatively function to displace any tissue from within the lumen, such as hyperplasia 106 (tissue growth) that may have grown through struts of the stent. The expansion element may be coupled to the housing 110 or any suitable structure of the system, and is preferably configured to operate in an enlarged mode 122 and a collapsed mode 124. The operation between the enlarged and collapsed mode is preferably selectively controlled by a user (e.g., physician) from outside the body of the patient, but may additionally and/or alternatively be self-expanding. As shown in FIG. 3, in the enlarged mode 122, the expansion element 120 radially expands, such that when the expansion element is positioned within the passageway 104 proximal and/or distal to the stent, the enlarged expansion element creates a tapered annular space 142 between the stent and passageway, or other suitable separation between the stent and passageway. The expansion element 120 preferably expands to a diameter larger than the diameter of the stent. However, the expansion element may additionally and/or alternatively expand to a diameter equal to the diameter of the stent, or any suitable diameter. For example, the expansion element may be biased to expand in one direction by an amount sufficient to separate at least one side of the passageway wall from the stent, while maintaining an overall size that is smaller than the stent. The expansion element 120 may be expandable continuously along a range, or may expand in discrete increments. In the collapsed mode 124, the expansion element 120 radially contracts, such as to allow the passageway 104 to return to its original diameter and/or allow the plurality of members 140 to advance past the expansion element 120.

Figure 5A:
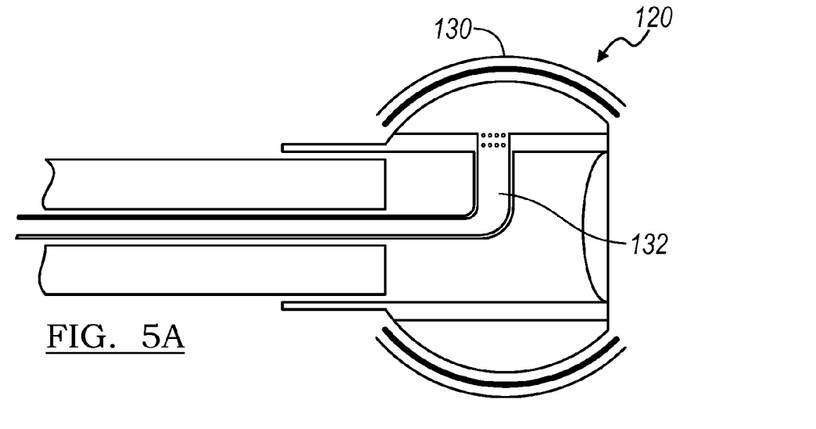
FIGS. 5A-5C are schematics of a longitudinal cross-sectional view, an axial cross-sectional view, and a zoomed partial view of an axial cross-sectional view, respectively, the expansion element.
Figure 5B:
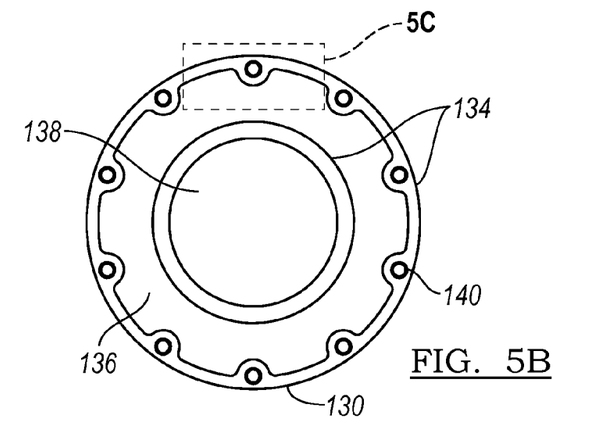
Figure 5C:
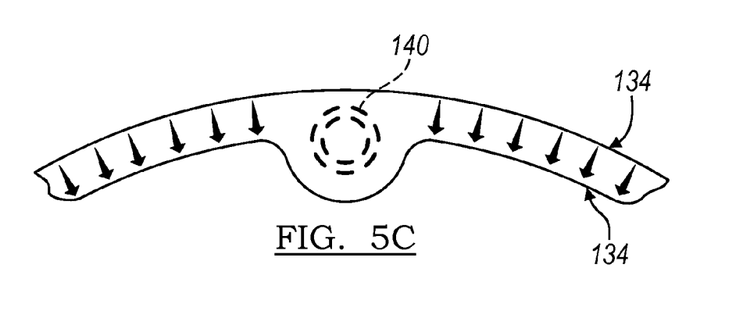

The expansion element 120 may include one or more of several variations of expanding mechanisms. In a first variation, as shown in FIG. 5, the expansion element includes a balloon 130 that is selectively inflatable, such that in the enlarged mode 122 the balloon is at least partially inflated and in the collapsed mode 124 the balloon is at least partially deflated. The selective inflation may utilize a tube through which air or another fluid is passed into the balloon 130. For example, as shown in FIG. 5A, an inflating tube 132 may pass from an external source (e.g. pump or syringe), through the passageway, and into the balloon 130, such that the user can externally control the inflation of the balloon. In one example, the balloon 130 is a sac that receives a fluid. In another example, the balloon 130 includes two or more sheets 134 of flexible material (e.g. elastomer) that are sealed together around a perimeter to form a cavity 136 that receives a fluid. As shown in FIGS. 5B and 5C, a cavity between the sealed sheets 134 (or within any other inflatable structure) may accommodate other structures, such as some or all of the plurality of members 140. Furthermore, the balloon may include multiple cavities interspersed between sealed sheets, such that different cavities allow discrete levels or selected locations of inflation.

Figure 6A:
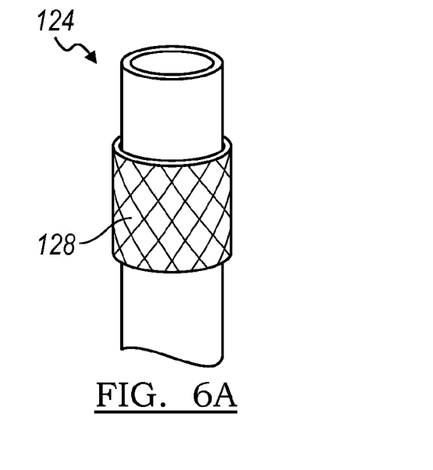
FIGS. 6A and 6B are schematics of a variation of the expansion element in collapsed and enlarged modes, respectively.
Figure 6B:
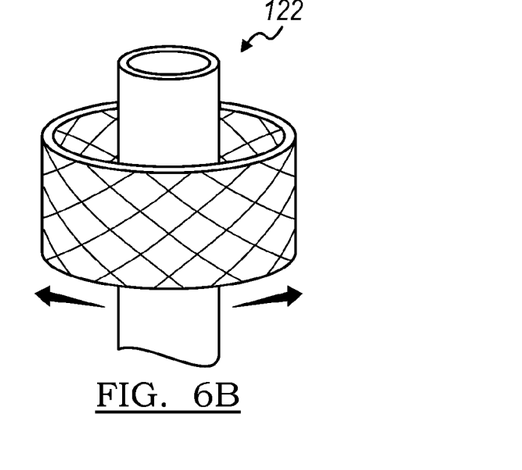

In a second variation, as shown in FIGS. 6A and 6B, the expansion element 120 includes an expanding linkage system 128. For example, the expanding linkage system may include scaffolding that selectively enlarges circumferentially. The expanding linkage system may include webbing or other connective material that helps distribute expansion forces across a greater surface area along the passageway. The expanding linkage system may be selectively controlled by a user outside the body, and/or be self-expanding, such as with temperature-dependent material. The expanding linkage system may be made out of nitinol, or another suitable biocompatible material.

In a third variation, the expansion element 120 includes a "wire hoop", including wire wrapped in a circular fashion to form a hoop with a lumen, with a trailing portion of the wire passing through the lumen, such that when the wire is pushed through the lumen, the hoop expands in circumference. In this variation, the trailing portion of the wire passes out of the passageway to outside the body, such the hoop expansion is selectively controlled by a user outside the body.

Although the expansion element 120 is preferably one of the above variations, the expansion element may include any combination of the variations, and/or include any suitable expanding mechanism. In any of these variations, as best shown in FIGS. 5 and 6, the expansion element may include a lumen 138 (e.g., the balloon 130 may be toroidal) such that other structures or objects may be passed through the lumen of the expansion element. Furthermore, in any of these variations, as shown in FIG. 7, the expansion element may include features to enhance displacement of any tissue within the stent lumen during enlargement of the expansion element, such a nub 139 on an external surface that pushes through a strut of the stent to displace hyperplasia.

Figure 8A:
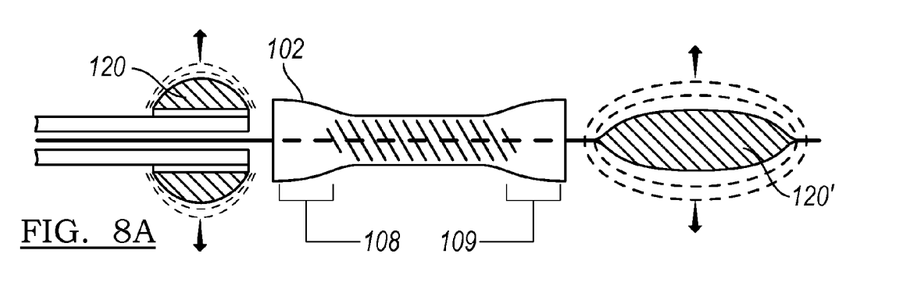
FIGS. 8A and 8B are schematics of a variation of the system of a preferred embodiment.
Figures 8B, 9A:
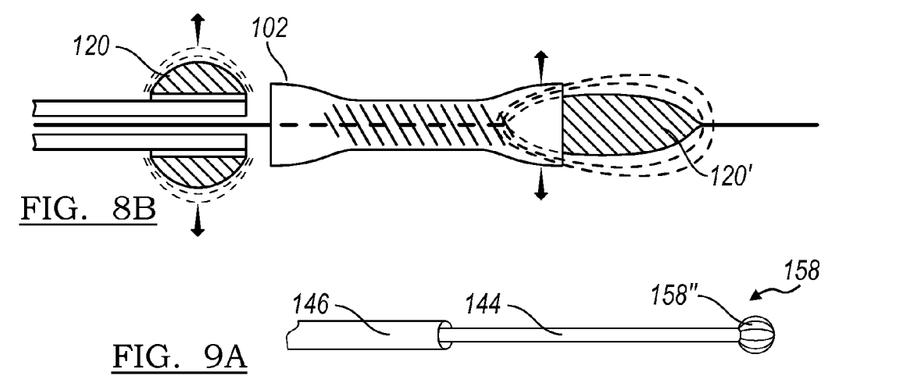
FIGS. 9A-9C are schematics of variations of the plurality of members in the system of a preferred embodiment.

In a preferred embodiment, the system includes a single expansion element 120, but other embodiments may alternatively include any suitable number of expansion elements. For example, as shown in FIG. 8, the system may include a proximal expansion element 120 that expands the passageway on a proximal end 108 of the stent and a distal expansion element 120' that expands the passageway on a distal end 109 of the stent. As another example, multiple expansion elements may be annularly layered over one another to allow for selective, incremental expansion. As yet another example, multiple expansion elements may be placed at different positions along the length of the housing 110 to enable more positional control for optimal enlargement of the passageway relative to the stent.

The plurality of members 140 function to engage and/or radially compress the stent. As best shown in FIGS. 1-3, the plurality of members 140 are preferably coupled to the housing 110, such as nested within the housing 110, and configured to advance or extend out of the housing to a location substantially longitudinally displaced (e.g. proximal and/or distal) from the expansion element, towards the tapered annular space 142 or other separation space between the stent and the passageway. In another variation, the plurality of members may additionally and/or alternatively be coupled to the expansion element, such that the members are pushed outwards toward the passageway wall when the expansion element is in its enlarged mode 122. In this variation, the plurality of members may advance or extend over, under, and/or through the expansion element towards the tapered annular space 142. When advanced outside the housing, the plurality of members 140 are preferably configured to be circumferentially distributed about the stent although the plurality of members may be distributed in any suitable manner. The plurality of members are preferably substantially radially contractible to allow at least partial radial compression of the stent and/or effective grasping of a non-compressible object in the passageway. The plurality of members preferably hold the stent in a compressed state while the stent is removed and/or repositioned. Furthermore, the radial contraction of the plurality of members may be reversible, such as to release the stent from its compressed state (e.g., for applications in which the stent is being repositioned within the patient). However, the plurality of members may additionally and/or alternatively be configured to engage the stent or other object in any suitable manner, such as with hooks, scoops, or adhesive.

The plurality of members 140 may advance to a position proximal and/or distal to the expansion element. In one variation in which the expansion element is positioned proximal to the implanted stent, the plurality of members may be advanced out of the housing to a location distal to the expansion element 120 to engage a proximal portion of the implanted stent. In another variation in which the expansion element 120 is positioned distal to the implanted stent, the plurality of members 140 may be advanced out of the housing to a location proximal to the expansion element to engage a distal portion of the implanted stent. In yet another variation, the plurality of members 140 may include some members that advance to a position proximal to the expansion element and some members that advance to a position distal to the expansion element. Furthermore, relative to the implanted stent, the plurality of members 140 may include some members that engage a proximal portion of the stent, some members that engage a central portion of the stent, and/or some members that engage a distal portion of the stent, or any suitable portion of the stent.

When advanced out of the housing towards the tapered annular space 142 or other separation space between the stent and the passageway, the plurality of members 140 may engage the stent in one or more various manners. In a preferred variation, the advanced members 140 are advanced into the tapered annular space 142 and are configured to receive and surround at least a portion of the stent. For example, as shown in FIGS. 1-2, the members 140 may be circumferentially distributed around an external surface of the stent. In another variation, the advanced members 140 may be inserted within the lumen of the stent, such that the members 140 are configured to engage an internal surface of the stent. In yet another variation, the advanced members engage both an external and internal surface of the stent. For example, the plurality of members may pinch or grasp a wall of the stent from the outside and the inside of the stent.

Figure 9B:
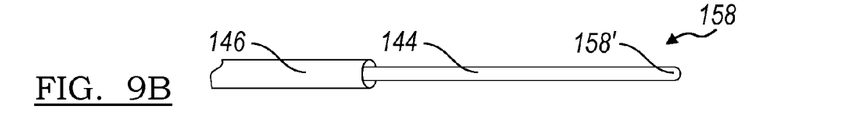
Figure 9C:
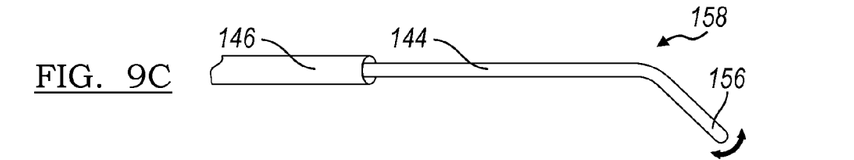

As shown in FIGS. 1-2, in a preferred embodiment, the plurality of members 140 include multiple wires 144 (e.g., similar to guidewires) that may be enclosed in one or more sheaths 146, such that the wires may be manipulated by the user from outside the body. The members 140 are preferably flexible, but the members may alternatively be any rigid, semi-flexible, or other suitable consistency such that the members may be manipulated to extend towards the stent (or grasp any suitable object in the passageway). As shown in FIG. 9, at least a portion of the members 140 may include an atraumatic tip 158 that avoids damage to the passageway walls, other tissue, or the stent. For example, the atraumatic tip may be a rounded atraumatic tip 158', include softer material, and/or include a cushioning element 158" such as an air- or fluid-filled sac at the end that absorbs impact.

Figure 4:
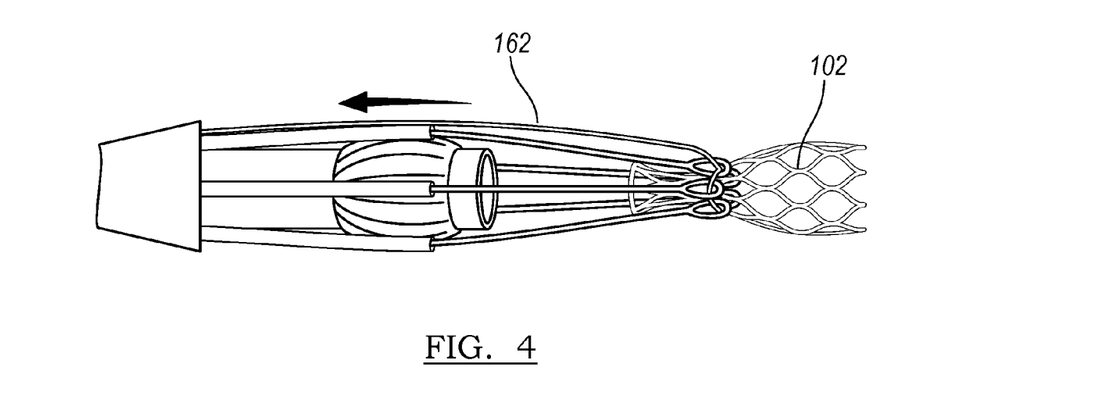
Figure 10:
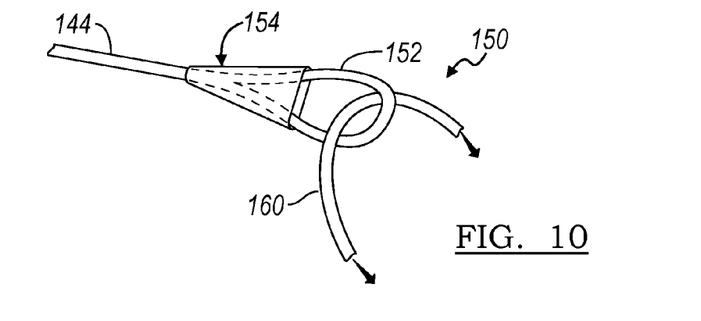
FIG. 10 is a partial schematic of a noose coupled to a member in the system of a preferred embodiment.
Figure 11A:
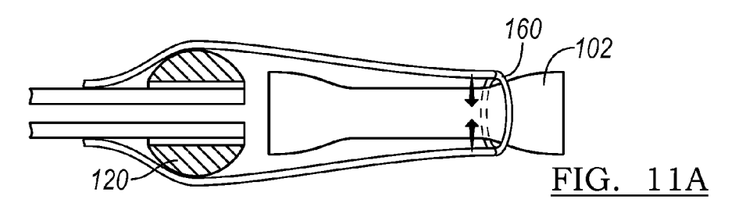
FIGS. 11A and 11B are schematics of a longitudinal cross-sectional view of a variation of the system of a preferred embodiment.
Figure 11B:
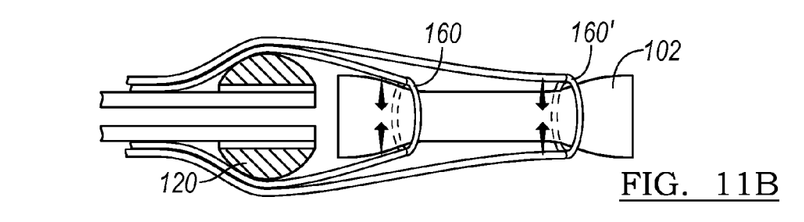

In a preferred embodiment, at least a portion of the members 140 may each include a distal end 150 with an aperture 152, (e.g., similar to the eye of a needle). For example, as shown in FIG. 10, a member may include a wire or other material that is bent back upon itself and secured with a fitting 154 to form an aperture 152. In this embodiment, as shown in FIGS. 4 and 10, the system may include a radially contractible noose 160 that is threaded through the apertures of the members, such that when the noose 160 is radially contracted, the noose gathers the distal ends of the members 140 at an approximate point. As shown in FIG. 11A, the noose forms a circumferentially tightenable loop that is configured to circumferentially surround and radially compress at least a portion of the stent. The noose 160 may be tightened and/or loosened by control of a pull line 162. For example, the pull line may be coupled to a mechanism manipulated by the user (e.g. a trigger) such that when the pull line 162 is activated, the noose encircling the stent contracts, thereby compressing the stent. Furthermore, as shown in FIG. 11B, the system may include two or more nooses that are longitudinally displaced from each other (e.g. a first noose 160 is proximal to a second noose 160'). In one variation, the nooses may be synchronized in operation, such that multiple nooses simultaneously radially compress to compress the stent at multiple locations along the length of the stent. In another variation, the nooses may be tightened in a particular sequence, such as progressively along the length of the stent (e.g., proximal nooses tightened before distal nooses) or depending on the position of the noose (e.g. nooses on the ends tightened before a noose located along the middle of the length of the stent). In either of these variations, the multiple nooses may be controlled by a single or multiple pull lines.

In one exemplary embodiment, as shown in FIGS. 1-3, each of the plurality of members 140 is a flexible wire disposed within a respective sheath, and are circumferentially distributed around the expansion element 120. Each of the members 140 may be advanced or extended at least partially out of the sheath. The distal ends of the members are threaded together by a wire forming a noose 160 or snare controllable by a pull line 162. As shown in FIG. 4, the noose may be contracted and gather the distal ends of the members 140 approximately at a single point. In the passageway during use, the members 140 are pushed outwards toward the tapered annular space 142 formed by the enlarged expansion element 120, such as by direct actuation of the members and/or by the enlargement of the expansion element. When the members 140 enter the tapered annular space, the members are positioned between the external surface of the stent and the passageway walls and the noose circumferentially surrounds the stent at a particular location along the stent length. The noose may then be tightened by pulling on the pull line, thereby radially compressing the stent and receiving at least a portion of the stent within the plurality of members (like a "cage") that help retain stent compression.

Figure 12A:
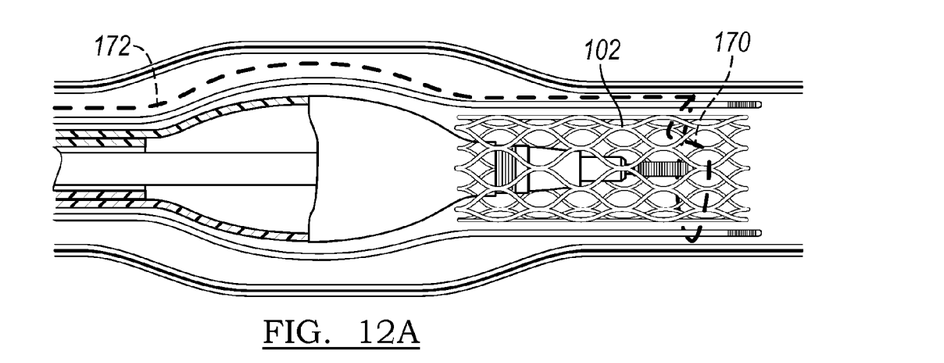
FIGS. 12A and 12B are schematics of an external cinch in the system of a preferred embodiment.
Figure 12B:
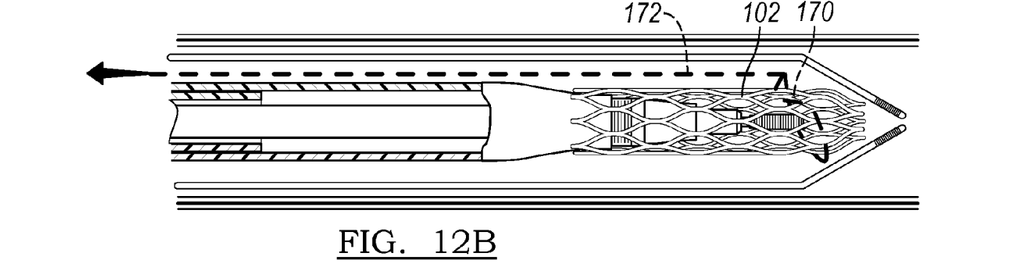

As shown in FIG. 12B, in an alternative embodiment at least one of the members 140 may include an articulated tip 156 that can be operated to radially compress or otherwise engage the stent. For example, the distal articulated end of members 140 may surround the stent and be cooperatively manipulated towards a common centerline of the system to compress the stent.

In some embodiments, the system may further include an external cinch 170, which may be similar to the noose 160, that supplements or replaces compression of the stent, or enhances grasping any suitable object. The external cinch 170 is preferably configured to circumferentially tighten around the stent to compress the stent, but may additionally and/or alternatively compress the stent by applying inward radial force from one, two, three, or any suitable discrete number of directions (e.g. pinching), or in any suitable manner. Furthermore, the external cinch may include features such as hooks, barbs, or adhesives to attach to the stent and/or any suitable portion of the system, or the external cinch may be integrated with a portion of the system in manufacture, such as by overmolding or thermal welding.

Figure 13A:
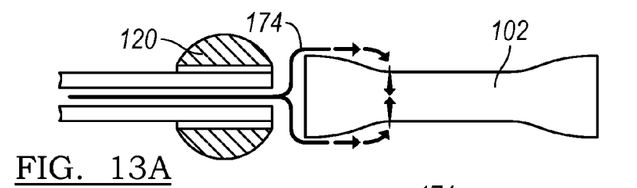
FIGS. 13A and 13B are schematics of alternative mechanisms to couple to an object in the passageway in the system of a preferred embodiment.
Figure 13B:
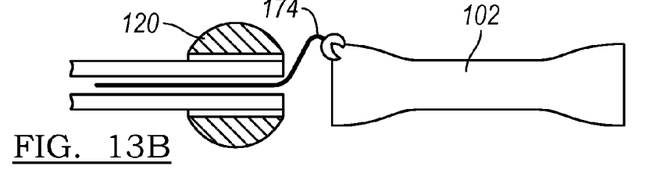
Figure 14:
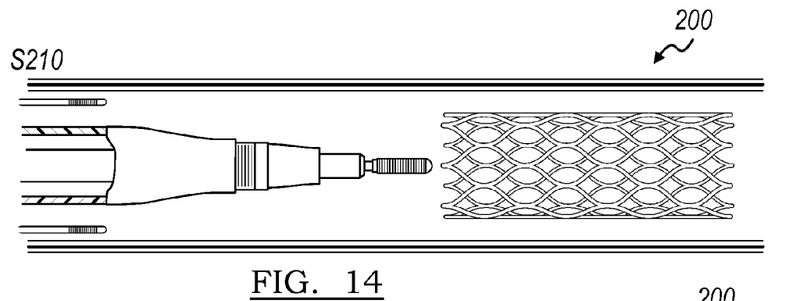
FIGS. 14-21 are schematics of steps of the method of a preferred embodiment.

The external cinch 170 may be one or more of several variations. In a first variation, the external cinch includes a radially compressible sheath that receives at least a portion of the stent. The sheath may be coupled to the plurality of members 140 such that when the members radially contract, the sheath correspondingly radially compresses, thereby compressing the stent. Alternatively, the sheath may be a separate mechanism that is passed separately over the stent (or within the lumen to couple to an internal surface of the stent) before radially compressing. In a second variation, the external cinch includes an elastic band that wraps circumferentially around the stent, such that the elastic band is expanded to experience enough stress to urge the stent in compression. Similar to the first variation, the elastic band may be coupled to the plurality of members or be a separate mechanism. In a third variation, as shown in FIGS. 12A and 12B, the external cinch 170 includes a loop that encircles around the stent and is controlled by a pull line 172. For example, the loop may be similar to the noose 160, except the loop is not coupled to the plurality of members and operates substantially independently of the plurality of members. In another example, the expanding linkage system or "wire hoop" variation of the expansion element 120 that is used to enlarge the passageway proximate to the stent may be used as a tightenable noose around the stent to compress the stent. In other variations, other mechanisms may engage and/or compress the stent in other manners, such as a clamp 174 that pinches outer surfaces (FIG. 13A) or an edge of the stent (FIG. 13B).

In some embodiments, the system may further include means for re-expanding the stent within the passageway, such as for applications in which the system is used to reposition the stent within the passageway. In one variation, the expansion element 120 may be further adapted to expand the stent from its compressed state. In another variation, the system may include a separate mechanism for re-expanding the stent. For example, the system may include a balloon that is advanceable into the lumen of the compressed state and inflates to expand the stent. However, any variations similar to the variations of the expansion element 120 may be used to re-expand the stent.

Method for Removing an Implanted Object

As shown in FIGS. 14-21, the method 200 for removing an implanted object from an initial location in a passageway of a preferred embodiment includes the steps of: positioning an expansion element S210 to a location proximate to the stent in the passageway; expanding the expansion element S220 at the location proximate to the stent, thereby creating a tapered annular space between the stent and the passageway; advancing a plurality of members toward the tapered annular space S230; engaging at least a portion of the stent with the plurality of members S240 such that the plurality of members are circumferentially distributed about the stent; radially contracting the plurality of members S250, thereby grasping or at least partially radially compressing the stent; and moving the stent from the initial location in the passageway S260. In one preferred embodiment, the method is used to remove and/or reposition a stent implanted in a gastrointestinal tract (such as the esophagus or intestines), but may alternatively be used to move a stent implanted in a cardiovascular, respiratory, or any suitable biological passageway. Alternatively, although the method is primarily described in terms of removing and/or repositioning a stent, the method may be used to remove and/or reposition any suitable foreign object from any suitable passageway or other environment.

Figure 15A:
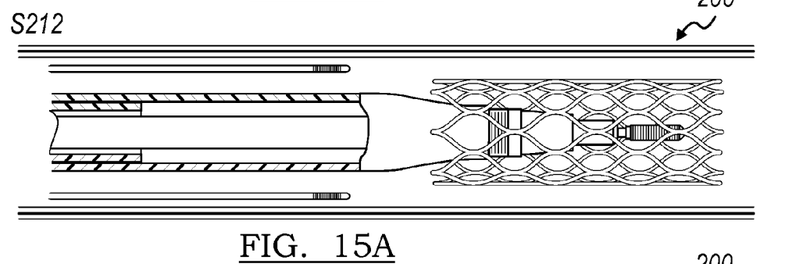
Figure 15B:
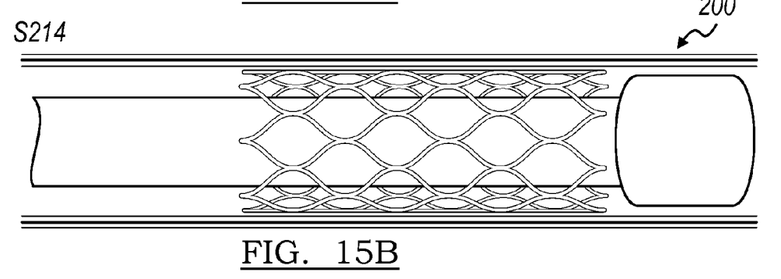

Positioning an expansion element in the passageway S210 functions to navigate the expansion element and other system components proximate to the stent. The expansion element may be positioned in the gastrointestinal tract, but may alternatively be positioned in any suitable biological or other passageway. The expansion element and other system components may be placed in the passageway with an endoscope, catheter, or other suitable navigational tool. In one variation, positioning the expansion element includes positioning an expansion element proximal to the stent S212 (FIG. 15A). In another variation, positioning the expansion element includes positioning an expansion element distal to the stent S214 (FIG. 15B).

Figure 16A:
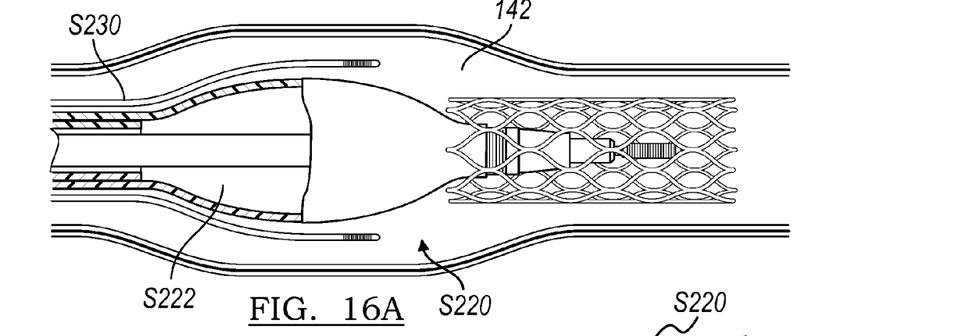
Figures 16B, 17A:
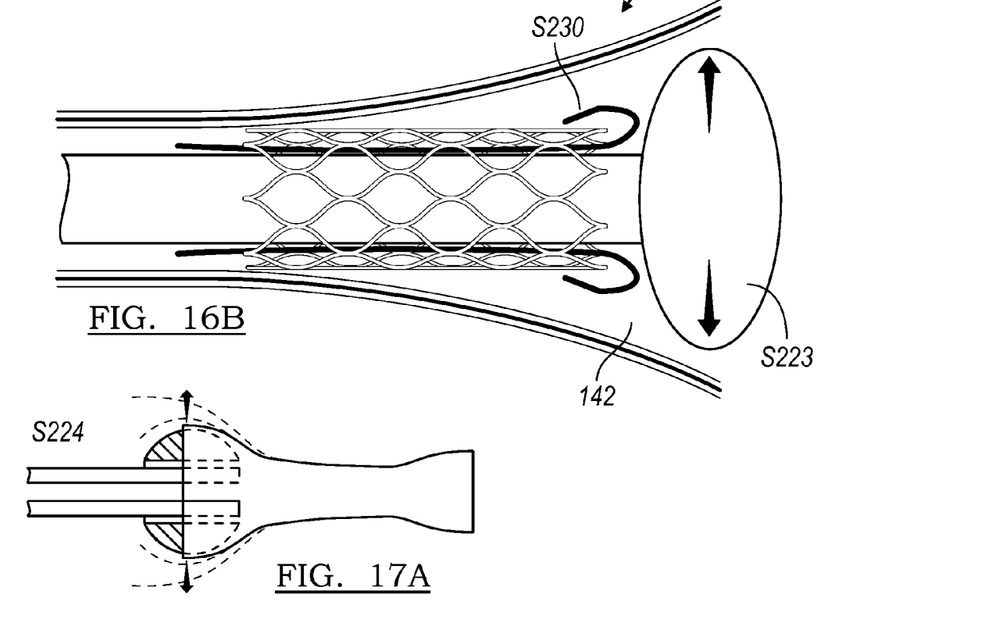

Expanding the expansion element S220 at the location proximate to the stent functions to form a tapered annular space or other separation space between the stent and the passageway, towards which the plurality of members is advanced to grasp and/or radially compress the stent. In one variation, expanding the expansion element includes expanding the expansion element to a diameter larger than the stent diameter. Expanding the expansion element may further include one or more of several steps. As shown in FIG. 16A, expanding the expansion element may include expanding the expansion element at a location proximal to the stent S222, such that the tapered annular space is between a proximal portion of the stent and the passageway. As shown in FIG. 16B, expanding the expansion element may include expanding the expansion element at a location distal to the stent S223, such that the tapered annular space is between a distal portion of the stent and the passageway. Furthermore, as shown in FIG. 8A, expanding the expansion element may include both expanding a expansion element at a location proximal to the stent and additionally expanding a expansion element at a location distal to the stent.

Figure 7A:
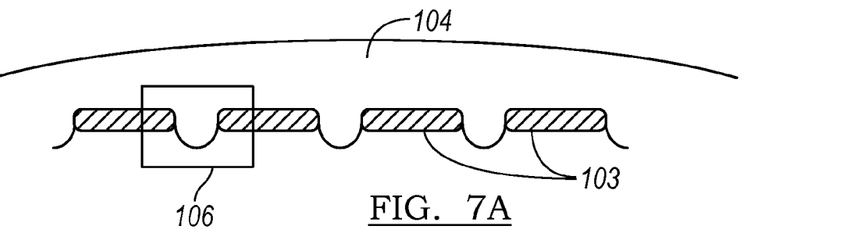
FIGS. 7A and 7B are schematics of the system used to displace tissue from within the lumen of a stent.
Figure 7B:
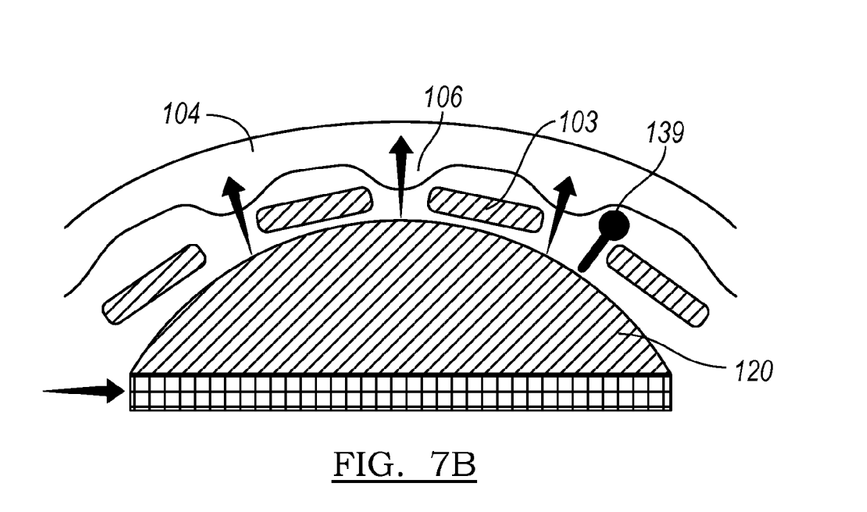
Figure 17B:
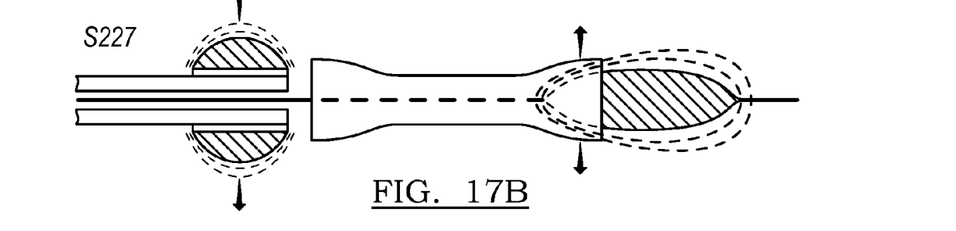

In another variation, expanding the expansion element S220 may additionally and/or alternatively include expanding the expansion element within the stent lumen S224, thereby displacing any tissue from within the stent. For example, as shown in FIGS. 7A and 7B, enlarging the expansion element from inside the stent may help remove hyperplasia 106 in passageway tissue that has grown through struts of the stent, by "pushing out" the ingrown hyperplasia 106 away from the stent. As shown in FIG. 17A, expanding the expansion element within the stent lumen may include expanding the expansion element within a proximal portion of the stent lumen S226. As shown in FIG. 17B, expanding the expansion element within the stent lumen may include expanding the expansion element within a distal portion of the stent lumen S227. Expanding the expansion element may include both expanding an expansion element within a proximal portion of the stent and expanding an expansion element within a distal portion of the stent.

The method may include any combination and permutation of these expanding steps. For example, any of the variations of expanding the expansion element within the stent lumen may be performed before and/or after expanding the expansion element at a location proximal and/or distal to the stent. Furthermore, some or all of these steps may be performed with the same single expansion element, or different expansion elements.

Figure 18:
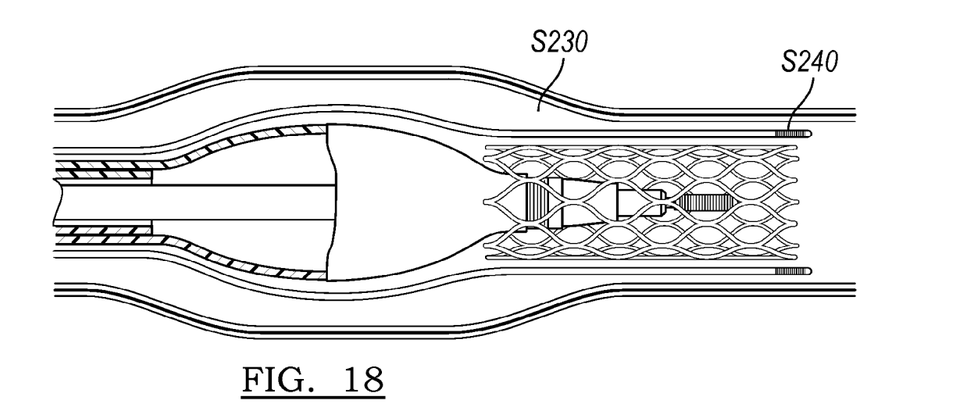

Advancing a plurality of members toward the tapered annular space S230 functions to position the plurality of members to engage with the stent. Advancing the plurality of members may be performed before, simultaneously with, or after expanding the expansion element. In a preferred variation, as shown in FIG. 18, advancing the plurality of members includes advancing the plurality of members into the tapered annular space or other separation space between the stent and the passageway. However, in alternative variations the plurality of members may not physically enter the separation space. For example, the plurality of members may be advanced toward the separation space but enter the stent lumen instead of the separation space.

Engaging at least a portion of the stent with the plurality of members S240 functions to couple at least some of the plurality of members to the stent for removal and/or repositioning. As shown in FIG. 18, engaging at least a portion of the stent preferably includes engaging an external surface of the stent with the plurality of members, such as by receiving the stent within the plurality of members such that the plurality of members are circumferentially distributed around the stent. However, engaging at least a portion of the stent may include engaging an internal or other suitable surface of the stent with the plurality of members.

Figure 19:
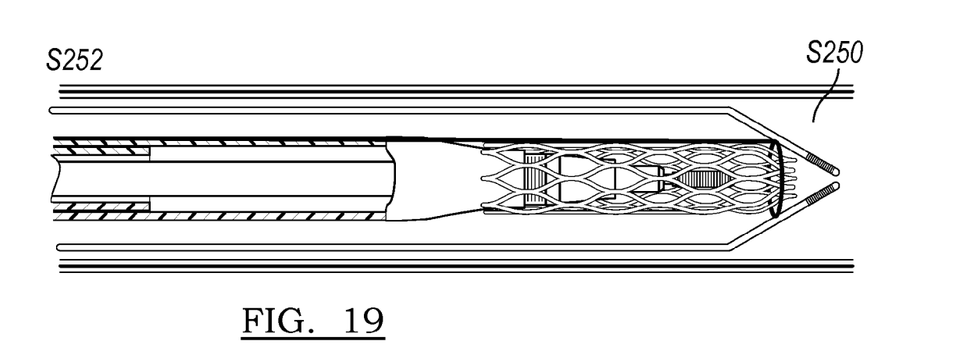
Figure 20:
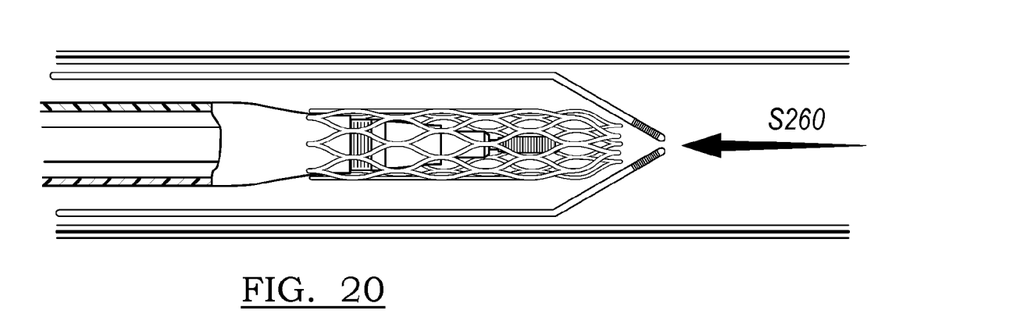

Radially contracting the plurality of members S250 functions to at least partially radially compress the stent. In a preferred embodiment, as shown in FIG. 19, radially contracting the plurality of members includes radially contracting a noose around the stent S252. As described above, the noose may be coupled to the plurality of members such that the radial contraction of the noose and the members is substantially simultaneous. Furthermore, radial contraction of the members may result in radial contraction of the noose, radial contraction of the noose may result in radial contraction of the members, or a third action may separately result in the radial contraction both the noose and members. Radially contracting the plurality of members may further include radially contracting a second or additional nooses along the length of the stent. The multiple nooses may be substantially simultaneously radially compressed, or radially compressed in a particular sequence (such as depending on the position of each particular noose along the length of the stent). As shown in FIG. 20, radially contracting the plurality of members may additionally and/or alternatively include articulating a distal end of one or more of the members towards the centerline of the stent, thereby radially compressing the stent. The method may additionally and/or alternatively include actuating an external cinch such as a radially constricting sleeve, elastic band, separate noose uncoupled from the members, or any suitable cinch to supplement and/or replace the action of the radially contracting members to radially compress the stent. Radially contracting the plurality of members may further include collapsing (e.g. radially contacting or deflating) the expansion element.

Figure 21A:
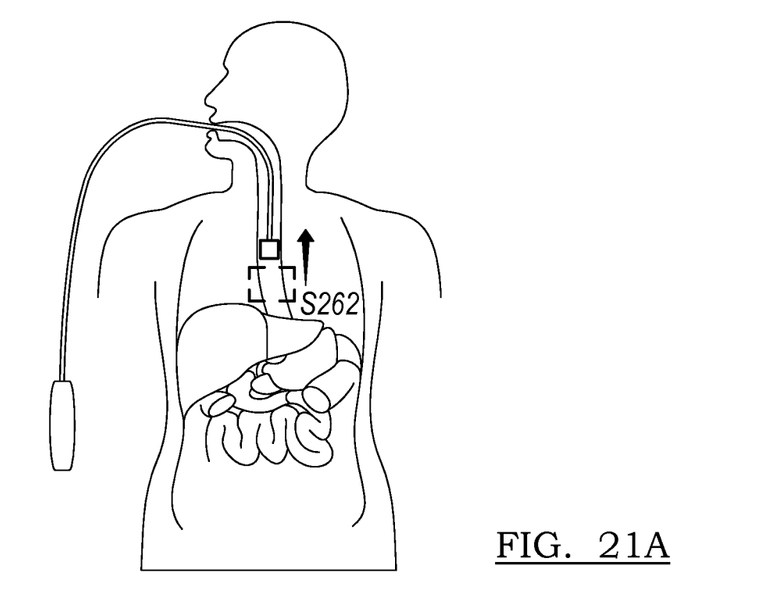
Figure 21B:
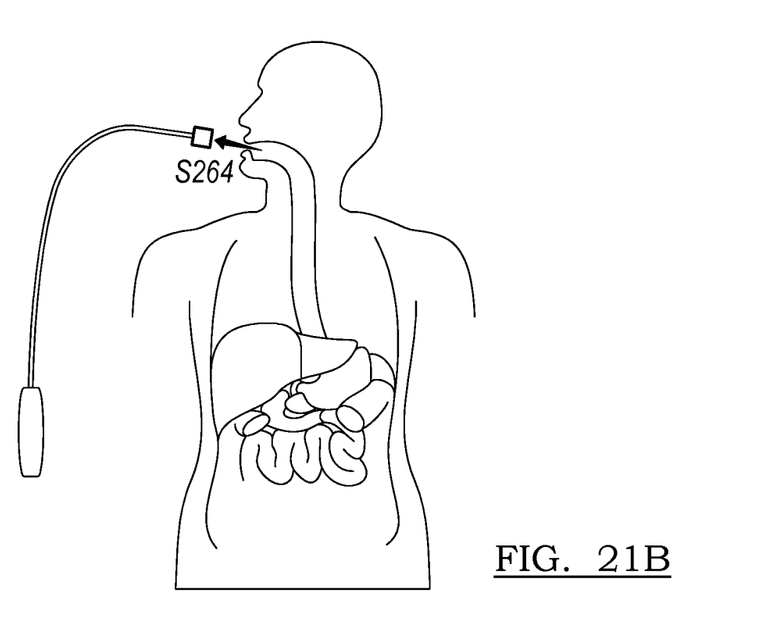

Moving the stent from the initial location in the passageway S260 functions to remove and/or reposition the compressed stent. In one variation, as shown in FIG. 21A, moving the stent includes depositing the stent at a second location in the same or other passageway S262. In this variation, the method may further include re-expanding the stent (e.g. with the expansion element or another means for stent expansion). In another variation, as shown in FIG. 21B, moving the stent includes withdrawing the stent from the passageway S264. In particular, the stent may remain compressed until the stent is removed from the passageway, and the stent may be fully removed from the patient.

As a person skilled in the art will recognize from the previous detailed description and from the figures and claims, modifications and changes can be made to the preferred embodiments of the invention without departing from the scope of this invention defined in the following claims.

We claim:

1. A method for moving an implanted stent having a stent lumen and a stent cross-sectional dimension from an initial location within a passageway in tissue in a patient, comprising:

positioning an expansion element to a location proximate to the stent in the passageway;

expanding the expansion element at the location proximate to the stent to create a tapered annular space between the stent and the passageway;

advancing a plurality of members towards the tapered annular space;

engaging at least a portion of the stent with the plurality of members, such that the plurality of members are distributed about the stent;

radially contracting the plurality of members, thereby at least partially radially compressing the stent; and moving the compressed stent from the initial location in the passageway.

2. The method of claim 1, wherein the act of positioning the expansion element in the passageway includes positioning the expansion element in the gastrointestinal tract.

3. The method of claim 1, wherein the act of expanding the expansion element includes expanding the expansion element at a location proximal to the stent, such that the tapered annular space is between a proximal portion of the stent and the passageway.

4. The method of claim 3, further including expanding an additional expansion element at a location distal to the stent, thereby creating a second tapered annular space between a distal portion of the stent and the passageway.

5. The method of claim 4, further including expanding the expansion element or the additional expansion element within the stent lumen, thereby displacing any tissue from within the stent lumen.

6. The method of claim 1, wherein the act of expanding the expansion element includes expanding the expansion element at a location distal to the stent, such that the tapered annular space is between a distal portion of the stent and the passageway.

7. The method of claim 1, wherein the act of expanding the expansion element includes expanding a balloon to a cross-sectional dimension larger than the stent cross-sectional dimension.

8. The method of claim 1, further including expanding the expansion element within the stent lumen, thereby displacing any tissue from within the stent lumen.

9. The method of claim 8, wherein the act of expanding the expansion element within the stent lumen includes expanding the expansion element against a proximal portion of the stent lumen.

10. The method of claim 9, wherein the act of expanding the expansion element within the lumen of the stent includes expanding the expansion element against a distal portion of the stent lumen.

11. The method of claim 1, wherein the act of advancing the plurality of members towards the tapered annular space includes advancing the plurality of members into the tapered annular space and wherein engaging at least a portion of the stent includes engaging an external surface of the stent with the plurality of members.

12. The method of claim 11, wherein the act of engaging the external surface of the stent includes receiving the stent within the plurality of members such that the plurality of members are distributed around the external surface of the stent.

13. The method of claim 12, wherein the act of radially contracting the plurality of members includes radially contracting a noose around the stent, thereby radially compressing the stent.

14. The method of claim 13, further including radially contracting a second noose around the stent, thereby radially compressing the stent.

15. The method of claim 14, wherein the act of radially contracting the first noose and radially contracting the second noose are performed substantially simultaneously.

16. The method of claim 1, wherein the act of engaging the at least a portion of the stent includes engaging an internal surface of the stent with the plurality of members.

17. The method of claim 1, wherein the act of moving the stent includes withdrawing the compressed stent from the passageway.

18. A method for moving an implanted object from an initial location within a passageway in a patient, the object having an object cross-sectional dimension, the method comprising:
  positioning an expansion element to a location proximate to the object in the passageway;
  expanding the expansion element to a cross-sectional dimension larger than the object cross-sectional dimension at the point proximate to the object, thereby creating a tapered annular space between the object and the passageway;
  advancing a plurality of members into the tapered annular space;
  receiving the object within the plurality of members such that the members are distributed about the object;
  radially contracting the plurality of members; and
  moving the object from the initial location in the passageway.

19. The method of claim 18, wherein the act of expanding the expansion element includes expanding the expansion element at a point proximal to the object.

20. The method of claim 19, further including expanding a second expansion element at a point distal to the object.

21. The method of claim 18, wherein the act of expanding the expansion element includes expanding the expansion element at a point distal to the object.

22. The method of claim 18, wherein the act of expanding the expansion element includes expanding a balloon to a cross-sectional dimension larger than the object cross-sectional dimension.

23. The method of claim 18, wherein the act of radially contracting the plurality of members includes radially contracting a noose, coupled to the plurality of members, around the object.

* * * * *